(12) United States Patent
Bertolino et al.

(10) Patent No.: US 6,946,092 B1
(45) Date of Patent: Sep. 20, 2005

(54) MEDICAL BALLOON

(75) Inventors: William Bertolino, Framingham, MA (US); Andrew J. Campbell, Reading, MA (US); Ralph Barry Jr., Hudson, MA (US); Nil Chay, Lynn, MA (US); Geraldo Carrion, Seabrook, NH (US); Shahen Andonian, Watertown, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 354 days.

(21) Appl. No.: 10/263,225

(22) Filed: Oct. 2, 2002

Related U.S. Application Data (63) Continuation of application No. 09/950,195, filed on Sep. 10, 2001, now abandoned.

(51) Int. Cl.7 .............................................. B29D 22/02
(52) U.S. Cl. ........................ 264/512; 264/515; 264/532; 264/535; 264/540; 264/570; 264/573
(58) Field of Search ................................ 264/512, 515, 264/532, 535, 540, 570, 573

(56) References Cited

U.S. PATENT DOCUMENTS

| | | | |
|---|---|---|---|
| 4,490,421 A | | 12/1984 | Levy |
| RE32,983 E | | 7/1989 | Levy |
| 4,917,667 A | | 4/1990 | Jackson |
| 4,963,313 A | | 10/1990 | Noddin et al. |
| RE33,561 E | | 3/1991 | Levy |
| 5,195,969 A | | 3/1993 | Wang et al. |
| 5,304,340 A | | 4/1994 | Downey |
| 5,306,246 A | | 4/1994 | Sahatjian et al. |
| 5,500,180 A | | 3/1996 | Anderson et al. |
| 5,714,110 A | | 2/1998 | Wang et al. |
| 5,797,877 A | | 8/1998 | Hamilton et al. |
| 5,879,369 A | * | 3/1999 | Ishida .................. 606/194 |
| 5,951,941 A | * | 9/1999 | Wang et al. .......... 264/523 |
| 6,017,324 A | | 1/2000 | Tu et al. |
| 6,210,364 B1 | | 4/2001 | Anderson et al. |
| 6,495,090 B1 | * | 12/2002 | Wilkins ................ 264/540 |

* cited by examiner

*Primary Examiner*—Suzanne E. McDowell
(74) *Attorney, Agent, or Firm*—Fish & Richardson P.C.

(57) ABSTRACT

Low polymer stress balloons are made by expanding a tube radially while allowing the ends of the tube to move axially in response to the radial expansion.

36 Claims, 10 Drawing Sheets

FIG. 11

MEDICAL BALLOON

This application is a continuation (and claims the benefit of priority under 35 U.S.C. § 120) of U.S. application Ser. No. 09/950,195, filed Sep. 10, 2001, now abandoned.

TECHNICAL FIELD

This invention relates to medical balloons, such as dilation balloons and catheters using such balloons, and methods of making and using the same.

BACKGROUND

Medical balloons can be deflated and inflated about their long supporting devices and placed in bodily conduits to administer treatments, for example, deployment of stents or widening of constricted passages during angioplasty, valvuloplasty, or urological procedures.

In angioplasty, for example, coronary angioplasty, a balloon can be used to treat a stenosis by collapsing the balloon and placing it in a bodily conduit, e.g., a coronary artery. The balloon is then inflated, e.g., by injecting a fluid, at a region of the artery that has been narrowed to such a degree that blood flow is restricted. Inflating the balloon can expand the stenosis radially so that the vessel will permit an acceptable rate of blood flow. This procedure can be a successful alternative, for example, to coronary arterial bypass surgery. After use, the balloon is deflated or collapsed and withdrawn.

Medical balloons can be manufactured by extruding a cylindrical tube of polymer and then pressurizing the tube while heating to expand the tube into the shape of a balloon. The balloon can be fastened around the exterior of a hollow catheter shaft to form a balloon catheter. The hollow interior of the balloon is in fluid communication with the hollow interior of the shaft. The shaft may be used to provide a fluid supply for inflating the balloon or a vacuum for deflating the balloon.

It is important that the balloon have a generally predictable shape on inflation. Typically, the balloon, such as a regular balloon, should have proximal and distal taper regions with closely matched taper angles and a uniformly cylindrical dilatation region. A deformed regular balloon, however, may have an irregular profile, such as a taper extending along the length of the dilatation region or portions with non-uniform cross sectional diameters. As a result, during use, deformed regular balloons may undesirably provide unpredictable, and thus unreliable, inflations/deflations or stent deployments. It is believed that deformed balloon shapes can be caused by locking the polymeric chains in undesirable configurations during manufacture, referred to as polymeric stress. The release or partial release of this stress, e.g., during heat sterilization, can also cause deformation.

SUMMARY

This invention relates to medical balloons, such as dilation balloons and catheters using such balloons, and methods of making and using the same.

In one aspect, the invention features a method of making medical balloons that relieves and minimizes stress in the balloon. The invention also features balloon devices such as, for example, balloon catheters and stent deployment systems.

In another aspect, the invention features a method of making a medical balloon including providing a polymer tube having two ends and suitable for being formed into the medical balloon, and expanding the tube radially while allowing the ends of the tube to move axially in response to said radial expansion. The method can further include axially orienting a material of the tube, e.g., by axially drawing the tube. Axially orienting the material can further include internally pressurizing the tube.

In another aspect, the invention features a method of making a medical balloon including providing a polymer tube having two ends and suitable for being formed into the medical balloon, drawing the tube axially, and expanding the tube radially while allowing the ends of the tube to move axially in response to said radial expansion.

Embodiments of aspects of the invention may include one or more of the following features. The ends of the tube are allowed to move freely as the balloon is formed. In some embodiments, the ends of the tube moves inwardly, for example, a distance between about 1 and about 40 percent, e.g., between about 5 and about 30 percent of an original length of the tube, between about 10 and about 25 percent, or between about 15 and about 22 percent. The tube is below a glass transition temperature of a material of the tube during drawing, e.g., below about 100° C. The tube is internally pressurized during drawing.

Expanding the tube can include heating the tube, e.g., to a temperature about equal to or greater than a glass transition temperature of a material of the tube. The tube can be expanded to an expanded diameter of the balloon being made. In certain embodiments, the tube can be expanded to an expanded diameter about 1 to about 15 times, e.g., about 5 to about 9 times, larger than an unexpanded diameter of the tube, e.g., by introducing a gas into the tube. Expanding the tube can include simultaneously heating and pressurizing the tube. Expanding the tube can include positioning the tube into a mold, and simultaneously heating and pressurizing the tube. Expanding the tube can include contacting the tube with a liquid, e.g., one including water.

The tube can be formed of a polymer having regions of different hardness. The tube can include a block copolymer having hard segments and soft segments. The block copolymer can be a polyether-ester elastomer, a polyester elastomer, or a polyether block amide. The tube can include a material such as a polyester and a polyamide. The tube can be a multilayer tube, such as a coextruded tube having layers of different hardness. The tube can be formed of a polymer that is not a block copolymer.

The method can further include characterizing the balloon by birefringence.

The method can further include attaching the balloon to a catheter to form a balloon catheter device. The method can further include sterilizing the balloon, e.g., by heating the balloon between about 32° C. and about 60° C.

The method can further include attaching the balloon to a catheter to form a balloon catheter device and/or positioning a stent on the balloon.

In another aspect, the invention features medical balloon product made according to the above methods.

Embodiments of the invention include one or more of the following features. The medical balloon can include a block copolymer having a cylindrically-shaped region exhibiting a birefringence pattern of substantially parallel lines before and after an exposure to sterilization temperatures. In certain embodiments, the balloon can be exposed to about 32° C. to about 60° C. The cylindrically-shaped region can have a length between about 1.5 cm and about 14 cm and/or an outer diameter between about 2 mm and about 30 mm, e.g., about 2 mm and about 20 mm, or about 2 mm and about 12 mm. The polymer can have regions of different hardness, e.g., hard segments and soft segments. The block copolymer can include a material such as, for example, a polyether-ester elastomer, a polyester elastomer, a polyether block amide, a polyester, or a polyamide. The balloon can be formed of multiple layers, e.g., multiple coextruded layers having different or the same hardness.

Embodiments may have one or more of the following advantages. During balloon formation, the balloon is not constrained in movement or axially drawn. Instead, the balloon is allowed to recover or relax, e.g., contract and/or expand axially and radially. As a result, the balloons can be formed uniformly and with a minimal level of residual stress. Subsequently, the balloons can then be exposed to a post-formation heat treatment, such as sterilization at temperatures of about 32° C. to about 60° C., without incurring substantial irregularities or deformations. The balloons can be produced consistently and predictably, thereby providing reliable results during use. The balloons may also be mechanically stable and have enhanced properties, such as burst strength and hoop strength. The method can also be performed without the need for certain production steps, such as annealing, thereby reducing manufacturing cost and time. The process can be useful for forming relatively large size balloons. The process can be useful for forming balloons about 1.5–14 cm or more in length and/or about 1–30 mm, e.g., about 1–20 nm, or about 1–12 mm, or more in diameter, where small amounts of residual polymeric stress may be manifested as relatively large physical deformations. Other balloon sizes are possible.

Other features and advantages of the invention will be apparent from the description of the preferred embodiments thereof and from the claims.

DETAILED DESCRIPTION

Figure 1:
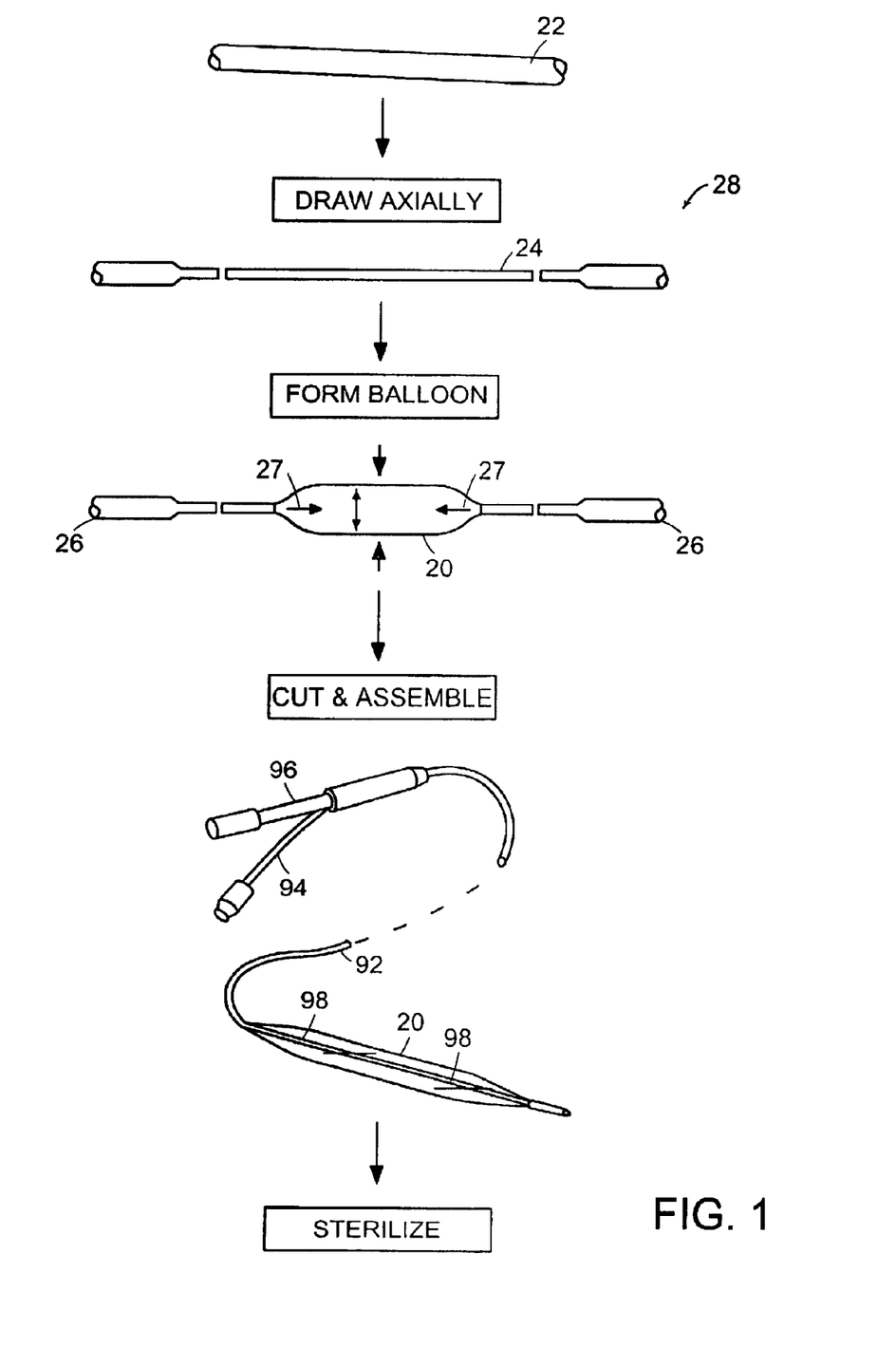
FIG. 1 is a schematic of an embodiment of a method of making a medical balloon.

Referring to FIG. 1, a method of fabricating a medical balloon 20 includes the steps of drawing a tube 22 axially to form a parison 28 having a stretched portion 24, and forming the balloon in the stretched portion. During formation of balloon 20, both ends 26 of parison 28 are allowed to move axially, e.g., contract in the direction of the balloon (shown by arrows 27). The balloon exhibits no or relatively small undesirable deformation, both after formation and after a post-formation heat treatment, such as heat sterilization in ethylene oxide. Consequently, the balloon provides enhanced performance. In certain embodiments, the balloon exhibits accurate sizing, good abrasion resistance, and/or consistent deflations and inflations.

Figure 2A:
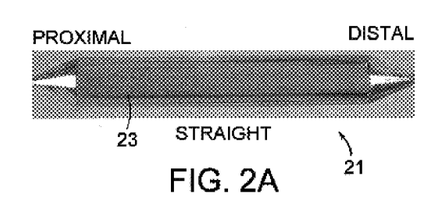
FIG. 2A is a photograph of a medical balloon having a substantially straight birefringence pattern.
Figure 2B:
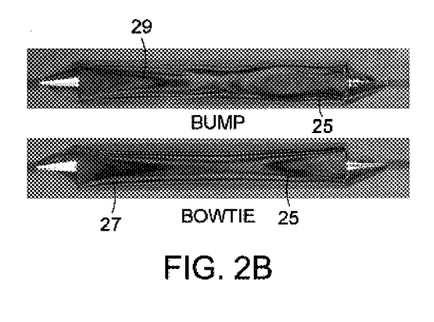
FIG. 2B is a photograph of medical balloons having a "bump" birefringence pattern and a "bowtie" birefringence pattern.
Figure 2C:
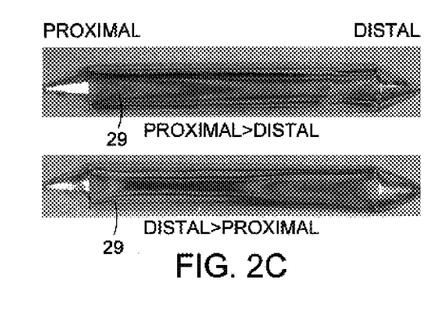
FIG. 2C is a photograph of medical balloons having a proximal to distal taper birefringence pattern and a distal to proximal taper birefringence pattern.

The amount of residual stress retained by a balloon can be measured by observing the birefringence of polarized light passing through the balloon. Referring to FIG. 2A, one example of a balloon in which stress has been substantially relieved can exhibit a birefringence pattern of generally parallel lines 23 across the dilatation portion, or body, 21 of the balloon and generally symmetric taper birefringence. Referring to FIGS. 2B and 2C, a balloon in which stress is retained can show wavy-line birefringence 25, asymmetric split line birefringence 27, and birefringence lines 29 that are not parallel with the cylindrical surfaces of the balloon. Upon release of this stress, e.g., by heat sterilization, the balloon may deform unpredictably into an undesired shape.

Without wishing to be bound by theory, it is believed that the deformed shapes in medical balloons can be the result of residual stresses imposed in the polymer during manufacture, e.g., during blowing and heating. Irregular balloon shapes can be particularly problematic when the balloons are formed of a material having molecular portions or segments capable of having different physical properties.

For example, a block copolymer can include molecular segments that are relatively hard or rigid and other segments that are softer or more elastic. The rigidity of the hard regions is believed to be caused by the intermolecular interaction of the polymer chains in these regions, which lock the segments in a particular orientation. In the soft segments, on the other hand, the molecular chains are more mobile, e.g., they can expand or contract. The sections can distribute themselves differently in response to stretching and temperature changes.

In forming a balloon, a portion of a tube of block copolymer is heated, typically above the glass transition temperature ($T_g$) of the tube material, and the polymer is stretched, e.g., radially, by blowing. This process orients the polymer. As the polymer is cooled, the chains become locked in given orientations.

In the present technique, the ends of the polymer tube are free to contract, expand, etc. as the inflated portion is formed so that the polymeric chains are able to orient in desirable configurations, thus reducing polymeric stress. In addition, in some embodiments, it is preferred that the tube is axially stretched and plastically deformed at low temperatures prior to blowing. The low temperature stretching is believed to axially orient the polymer. By carrying this step out at low temperatures, e.g., less than $T_g$, the polymer orientation is not modified by heat-induced phenomena. As a result, the balloon is biaxially oriented with reduced stress.

Balloon 20 can be formed of a resilient material, such as a polymer, that is capable of being inflated and deflated in a patient. Preferably, the material is relatively stable upon crystallization. As discussed above, the method is particularly applicable to polymers or polymer combinations in which stress produced during manufacture is subsequently released, e.g., during heat sterilization. Deformation problems can be most severe when soft polymers are used in combination with hard or rigid, highly crystalline polymers, such as polyethylene terephthalate (PET). For example, block copolymers having soft and rigid blocks or combinations of different polymers in coextruded layers having different stress release characteristics can be effectively manufactured with reduced deformations. Examples of suitable materials include block copolymers such as a polyetherester elastomer (e.g., Arnitel® EM740, from DSM Engineering Plastics, Evansville, Ind.), a thermoplastic polyester elastomer resin (e.g., Hytrel® from E. I. du Pont de Nemours and Co.), or a polyether block amide (e.g., Pebax® from Atofina). Other materials can also be used, for example, organic or synthetic polymers such as polyimides, nylons, rubbers, latex, or engineered resins. In some embodiments, the material can have a hardness, measured in Shore D hardness, between about 50 and about 75.

Figure 3A:
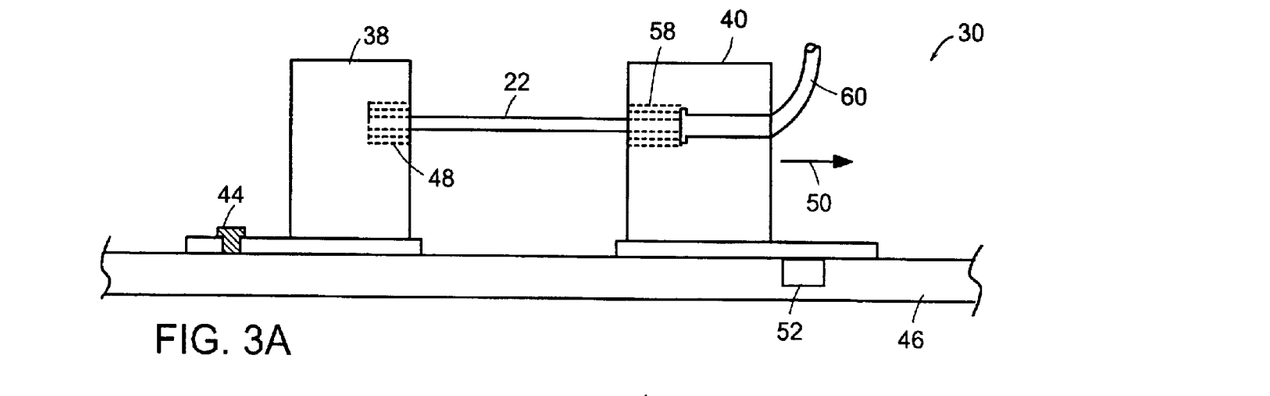
FIGS. 3A–3B are schematic views of an embodiment of a drawing machine during use.
Figure 3B:
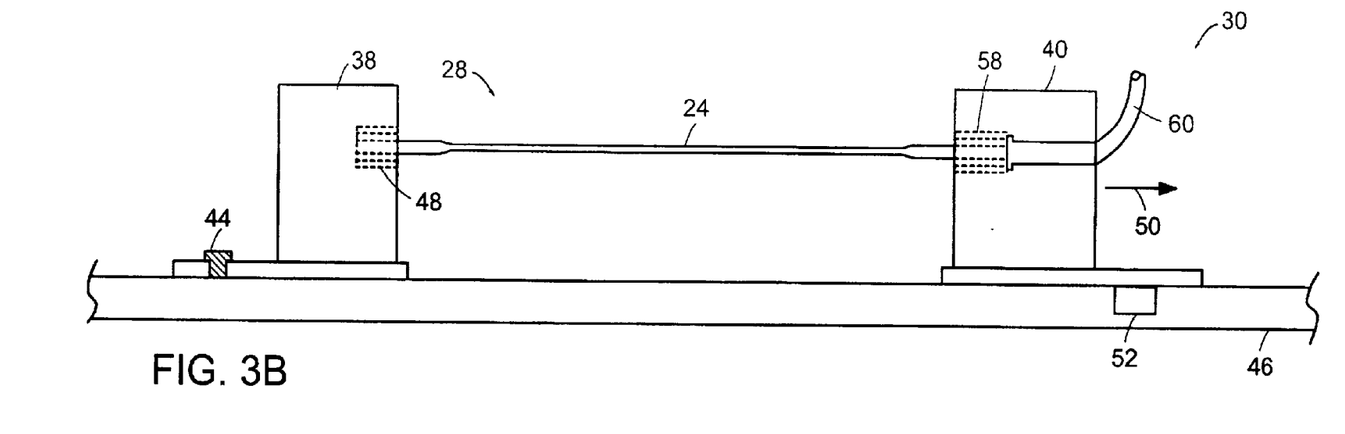

Referring to FIGS. 3A and 3B, in one embodiment, parison 28 may be formed in a drawing machine 30. Drawing machine 30 stretches tube 22, which axially orients the polymer. The stretching preferably is done below the glass transition temperature of the polymer, e.g., at room temperature (typically about 15 to about 30° C.), so the parison is not exposed to high temperatures during stretching. Drawing machine 30 includes a pair of opposed gripping assemblies 38, 40 between which tube 22 can be stretched. Gripping assembly 38 is fixed, e.g., using a bolting arrangement 44, to a support table 46 and includes a pressured tube gripper 48 that clamps a sealed end of tube 22. Gripping assembly 40 is moveable. Assembly 40 can be translated along table 46 (arrow 50) by coupling the assembly to a translation device 52, such as a planetary gear coupled to a servo motor. Moveable gripping assembly 40 includes a pressurized gripper 58 that grips an open end of the tube 22 and permits a coupling 60 for introduction of pressurized fluid, such as a gas, from a fluid source into the tube. Suitable grippers are available from, for example, SMC Corp., Indianapolis Ind. (Model MGQ2-25S). The servo motor and gas source may be interfaced to a computer to draw an end of tube 22 a predetermined distance at a predetermined rate while providing a predetermined pressure profile. Multiple sets of gripper assemblies may be arranged in adjacent rows to simultaneously stretch multiple tubes. Parison 28 may also be stretched by translating both ends 26. Pressurized gas may be introduced from both ends 26.

Tube 22 is generally a cylindrical member dimensioned to be suitable for being fabricated into a medical balloon. For example, tube 22 can have a length of about 5 cm to about 42 cm; an inner diameter of about 0.2 mm to about 3 mm; and an outer diameter of about 1 mm to about 4 mm, depending on the size of the balloon to be fabricated and the material of the tube. Other tube sizes can be used.

The dimensions of stretched portion 24, e.g., length, and end tapers, are a function of the drawing parameters, such as the rate of drawing, the distance of drawing, the initial dimensions of tube 22, the material of the tube, the internal pressure, inner diameter, and outer diameter. Generally, the larger the balloon to be fabricated, the more tube 22 is drawn and the longer the stretched portion. The rate of drawing can be relatively slow or relatively fast, e.g., about 0.02 cm/sec to about 0.6 cm/sec. Faster draw rates can improve production throughput.

The rate and distance of drawing are generally balanced with the applied internal pressure to form a substantially uniform stretched portion 24. Relatively low pressure is typically applied at relatively slow draw rates to avoid bulging stretched portion 24 and/or bursting tube 22. Conversely, at relatively high draw rates, relatively high pressure is applied to maintain the integrity of the lumen of tube 22 and to minimize crystallization in stretched portion 24, which could later appear as defects during balloon formation.

Figure 4A:
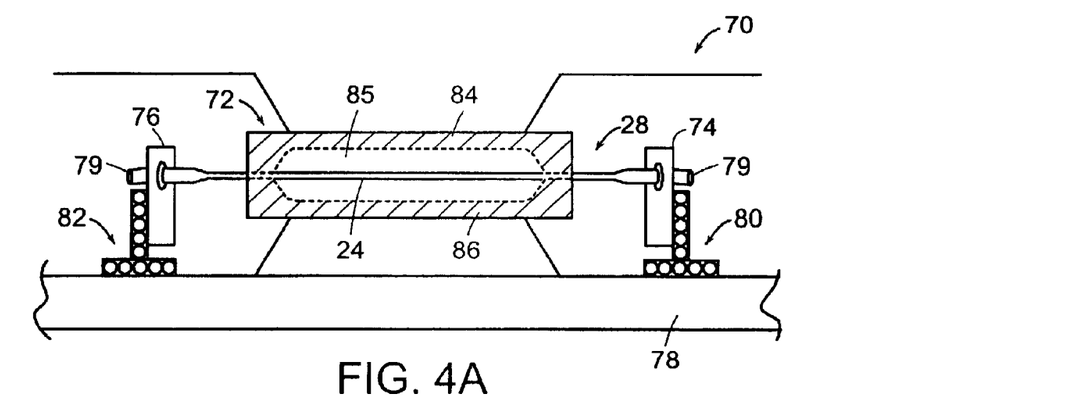
FIGS. 4A–4C are schematic views of an embodiment of a blow-molding assembly during use.
Figure 4B:
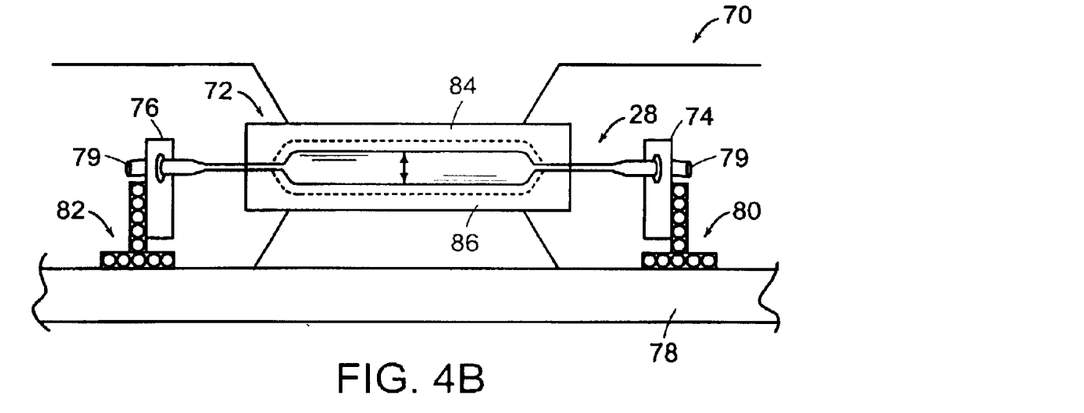
Figure 4C:
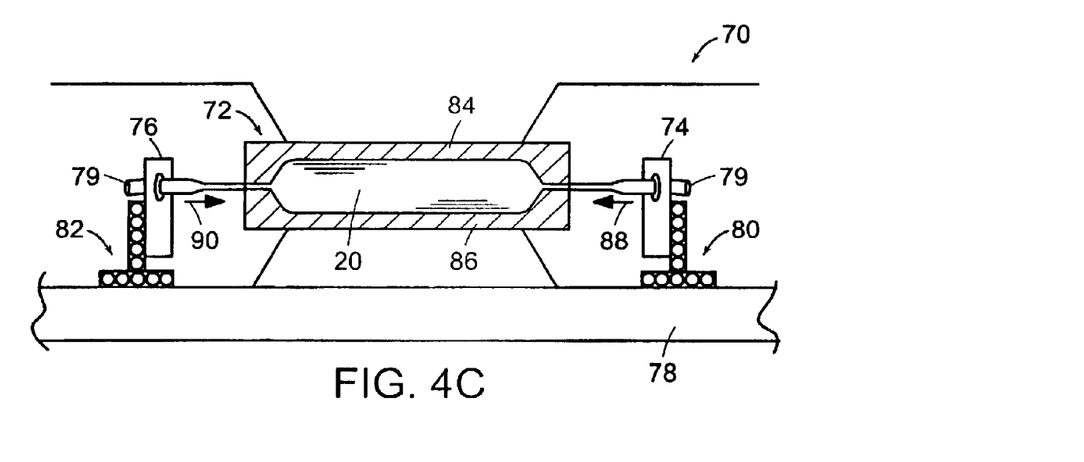

Referring to FIGS. 4A–4C, in one embodiment, parison 28 is formed into a balloon by expanding stretched portion 24 under pressure while heating. During expansion, both ends of parison 28 can contract axially to relieve stress introduced during the axial stretching or radial expansion. In one embodiment, balloon 20 can be formed using a blow-molding assembly 70, which includes a heated mold 72 and two opposing gripper assemblies 74, 76 that are translateably mounted on a support table 78 using low friction couplings 80, 82. The mass of the grippers and the low friction couplings 80, 82 are arranged to allow the parison to move freely or with minimal inhibition. In some embodiments, the mass of the grippers and the low friction couplings 80, 82 are arranged to provide a small frictional resistance, e.g., having a coefficient of friction of about 0.003, to axial motion compared to the force of the relaxing polymer. Suitable couplings include ball slides. In other embodiments, the ends of the balloon can be mechanically urged inwardly, e.g., using a motor to release stress.

Mold 72 may be a clamshell-type mold having an upper portion 84 and a lower portion 86 that can be positioned about stretched portion 24, and includes a mold cavity 85 of desired shape. Mold 72 can be made of any material that is stable, e.g., does not melt, at balloon forming temperatures and that can be heated, e.g., by an infrared lamp or by a resistive or inductive heater. Suitable materials include those with relatively high thermal conductivity such as, e.g., aluminum, stainless steel, beryllium copper alloys, and glass.

Gripper assemblies 74, 76 include pressurized grippers to grip the ends of the parison and couplings 79 to permit the introduction of pressurized gas. Throughout balloon formation, pressure is applied in the parison. The amount of applied pressure depends, for example, on the size of the balloon and the properties of the parison such as hoop stress. For example, larger balloons tend to require less pressure. Too much pressure can burst the balloon, while too little pressure can produce incomplete balloon formation.

To form balloon 20, parison 28 is positioned between gripper assemblies 74, 76 and mold 72 is positioned about the central portion of the parison (FIG. 4A). Mold 72 is then heated, typically above the glass transition temperature of the parison polymer(s), while pressurized gas is introduced into the parison lumen, causing the central portion of the parison to expand into the shape of the mold (FIG. 4B). As evident, the ends of the parison engaged by the grippers are not substantially heated. As the temperature of the mold is increased and the polymer heats above $T_g$ and is pressurized, stresses induced during blow molding and axial stretching are allowed to relax by permitting the ends of the parison to be drawn inward (arrows 88, 90) (FIG. 4C). The parison can axially relax between about 5 to about 30 percent of its length. The ends of the parison move inwardly during blowing since the grippers are mounted on low friction couplings 80, 82, which are slideable inwards. The stress release may be gradual as the balloon forms. Typically, the balloon expands to a diameter of about 5–9 times the inner diameter of tube 22. After reaching the desired diameter, mold 72 is cooled.

Referring again to FIG. 1, after formation of balloon 20, the balloon is cooled, the end portions are cut away, e.g., the portions extending outwardly from the smallest diameter of the parison, and the balloon is assembled upon a suitable catheter 92 that has a balloon inflation lumen 94 for inflation of the balloon and a through lumen 96 for receiving a guidewire. Radiopaque markers 98 can be provided on catheter 92 near the ends of the main body of balloon 20. Catheter 92, including balloon 20, can then be sterilized.

In other embodiments, balloon 20 can be used with a balloon expandable stent to form a stent delivery system. For example, the stent is crimped to its reduced diameter over a delivery catheter, positioned at a deployment site, and then expanded in diameter by fluid inflation of the balloon positioned between the stent and the delivery catheter.

In other embodiments, the step of axially drawing tube 22 can be eliminated. For example, tube 22 can be pre-formed axially oriented and/or include a segment having a diameter equal to stretched portion 24. Alternatively, a hypotube having an outer diameter equal to the inner diameter of stretched portion 24, can be inserted into tube 22 prior to axial stretching to maintain the lumen of the stretched portion.

In other embodiments, during axial drawing, both ends of tube 22 can be drawn. During balloon formation, the pressuring fluid can be introduced through only one end of parison 28. Other balloon formation techniques may be used. For example, free blowing without a mold may be used.

In some embodiments, mold 72 includes an indicator, e.g., a hash mark, that can be used to place parison 28 in the mold at a predetermined position. The indicator can minimize systematic error.

In other embodiments, the methods described above can be applied to other balloon configurations, such as, for example, step, or non-regular, balloons.

Further embodiments are illustrated in the following examples, which are not intended to be limiting.

EXAMPLE 1

Figure 5:
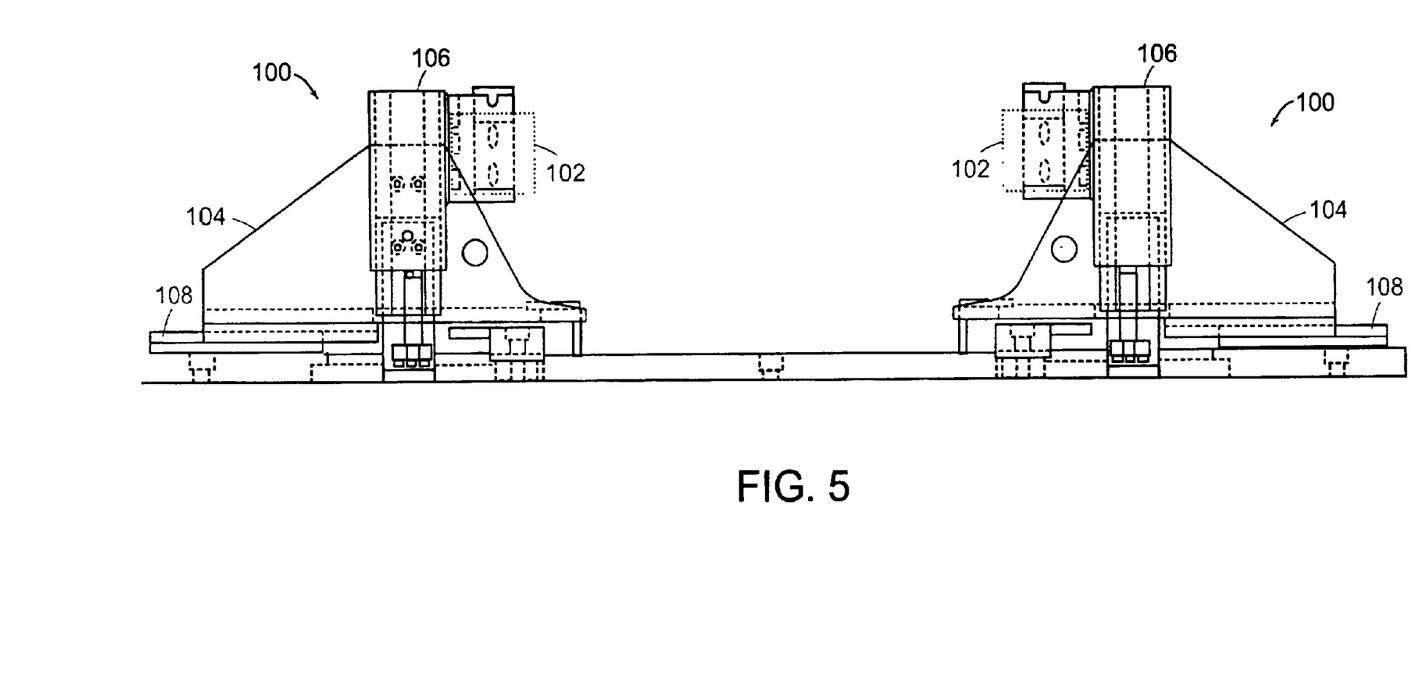
FIG. 5 is a front view of an embodiment of a gripper assembly.
Figure 6:
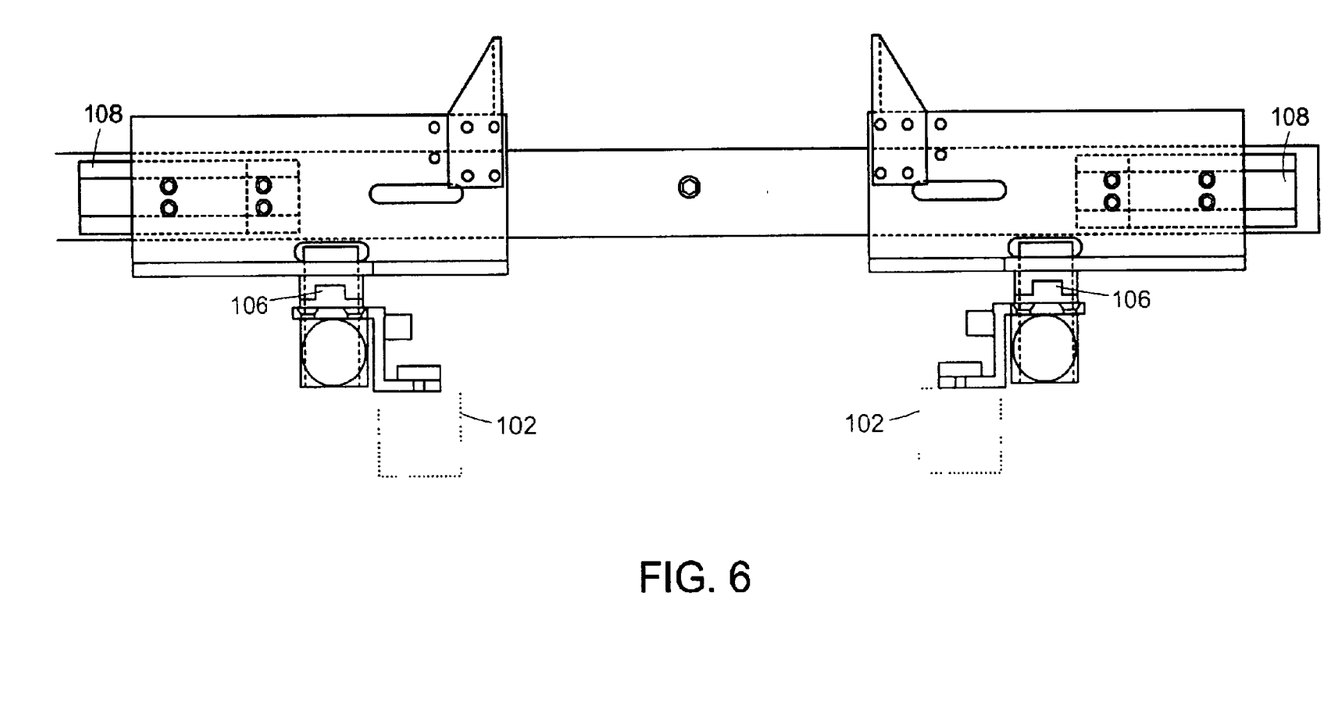
FIG. 6 is a top view of the gripper assembly of FIG. 5.
Figure 7:
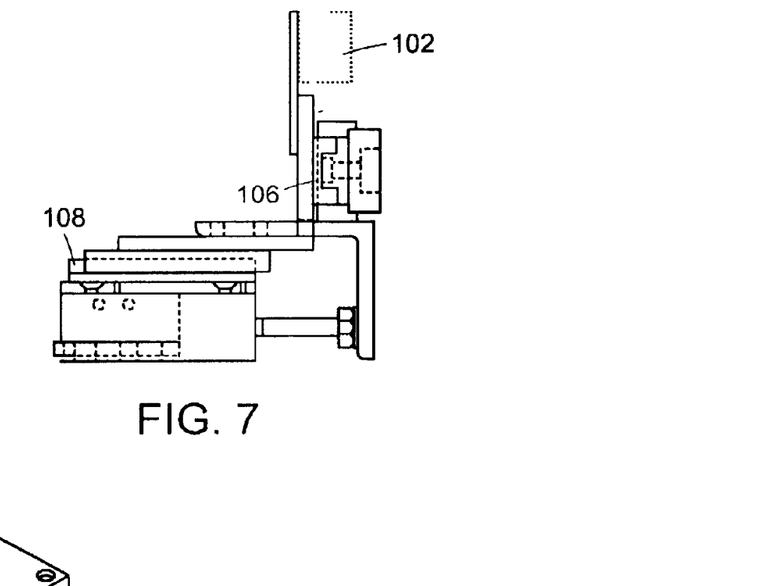
FIG. 7 is an end view of the gripper assembly of FIG. 5.

FIGS. 5–7 illustrate a particular gripper assembly and low friction coupling.

Each gripper assembly 100 includes a gripper 102 that is connected, e.g., by brackets 104, to a vertically-mounted ball slide, or crossed roller slide, 106 and a horizontally mounted ball slide 108. Each gripper 102 connects to one end of a parison and allows a pressurizing gas to be introduced into the lumen of the parison. Slides 106 and 108 allow the parison to move freely, e.g., contract axially and/or move vertically within a mold, during balloon formation. Slides 106 and 108 are commercially available from, for example, PIC Design Corp., Middlebury, Conn. (Part No. PNBT-1080A).

Figure 8:
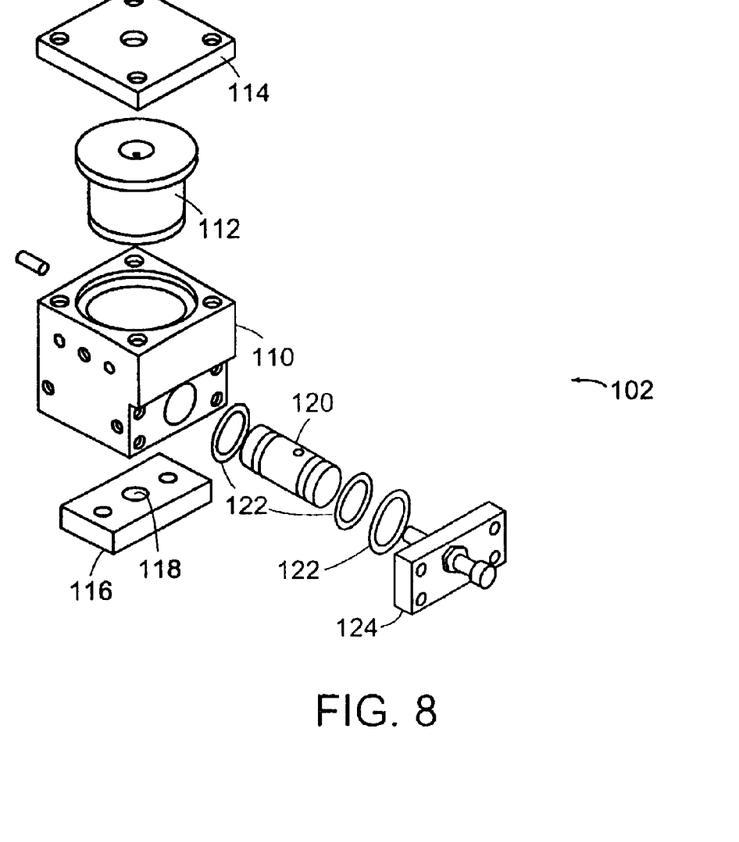
FIG. 8 is an exploded perspective view of an embodiment of a gripper.

Referring to FIG. 8, gripper 102 includes a cube-like housing 110. On a first face of housing 110, gripper 102 receives a silicone grommet 112 and a grommet cap 114. On a second face opposite the first face, housing 110 receives a balloon guide 116 having an opening 118 through which the parison is fitted. On a third face, housing 110 receives a piston 120, including O-rings 122, and a piston cap 124. Generally, gripper 102 mates with the ends of the parison by applying pressure to piston 120 to lock the parison in place. Simultaneously, pressure is applied around grommet 112 to allow the inflation pressure to flow into the parison without leaking.

EXAMPLE 2

The following illustrates formation of a 6-4 (i.e., 6 mm O.D. and 4 cm long) Arnitel® (EM740 from DSM Engineering Plastics, Evansville, Ind.) balloon.

Figure 9:
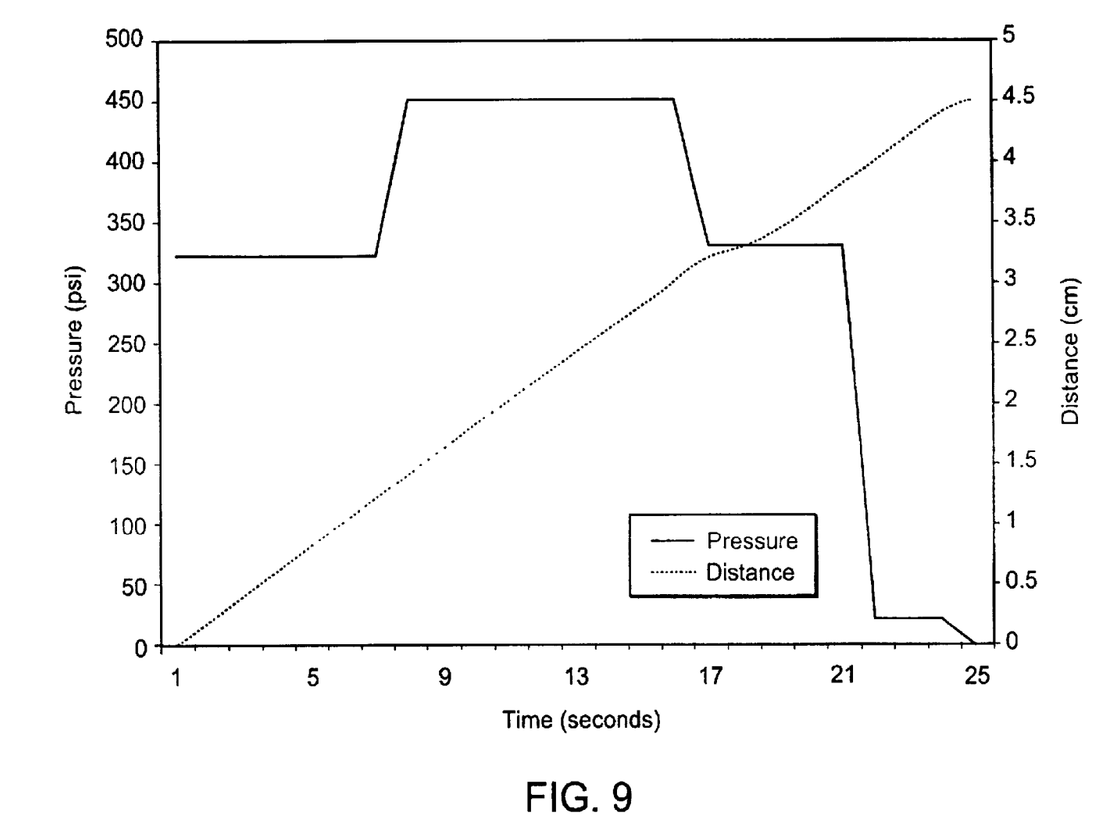
FIG. 9 is a plot of applied internal pressure (psi) vs. time (sec) during axial drawing of a 6-4 balloon.

A tube of Arnitel® was provided having an inner diameter of about 0.086 cm (0.034 in), an outer diameter of about 0.177 cm (0.07 in), and a length of about 30.48 cm (12 in). The tube was sealed on one end by heating and pressing the end with pliers. The tube was formed into a parison by axially drawing the open end of the tube at room temperature. The draw rate was about 0.41 cm/sec (0.16 in/sec); the draw length was about 10.16 cm (about 4 in); and the maximum internal nitrogen pressure was about 450 psi (FIG. 9). A stretched portion about 10.16 cm (about 4 in) long and having an O.D. of about 0.152 cm (0.06 in) was produced. The sealed end of the tube was removed.

The parison was formed into a balloon using an aluminum clamshell mold positioned between a gripper assembly described in Example 1. The lower half shell included a thermocouple positioned at the center to monitor the temperature of the mold during use.

Before forming the balloon, the lower half of the mold was sprayed with a liquid, such as water, until the lower half was uniformly coated. It is believed that the liquid acted as a surface lubricant for the balloon and/or a plasticizer for the polymer in the balloon. The liquid may also help to maintain a uniform heat profile along the mold. The parison was then placed on the lower half of the mold at a predetermined position, e.g., by placing an end of the parison at an indicator mark, and connected to the grippers. The horizontally-mounted ball slide allowed the parison to move horizontally within the mold. The upper half of the mold was then lowered onto the lower half. The parison was then pressurized by introducing $N_2$ gas into both ends of the parison, and heated to form the balloon. The parison was not drawn axially during balloon formation. Instead, the parison was allowed to move freely such that as the balloon was formed and needed more material to expand, the balloon drew adjacent material toward itself.

The parison was heated to balloon forming temperatures about equal to or greater than a glass transition temperature ($T_g$) of the parison material, e.g., about 45–50° C. for Arnitel®. Due to heat loss, e.g., radiative heat loss to air, the mold was heated to a temperature greater than the glass transition temperature of the parison material, e.g., about 110–115° C., as measured by the thermocouple positioned in the lower half of the mold. The parison was maintained at the balloon forming temperatures for a time sufficient for the balloon to fully form. Then, the heater was turned off, the mold was force quenched to room temperature by spraying the mold with water, and the upper half of the mold was lifted.

Figure 10:
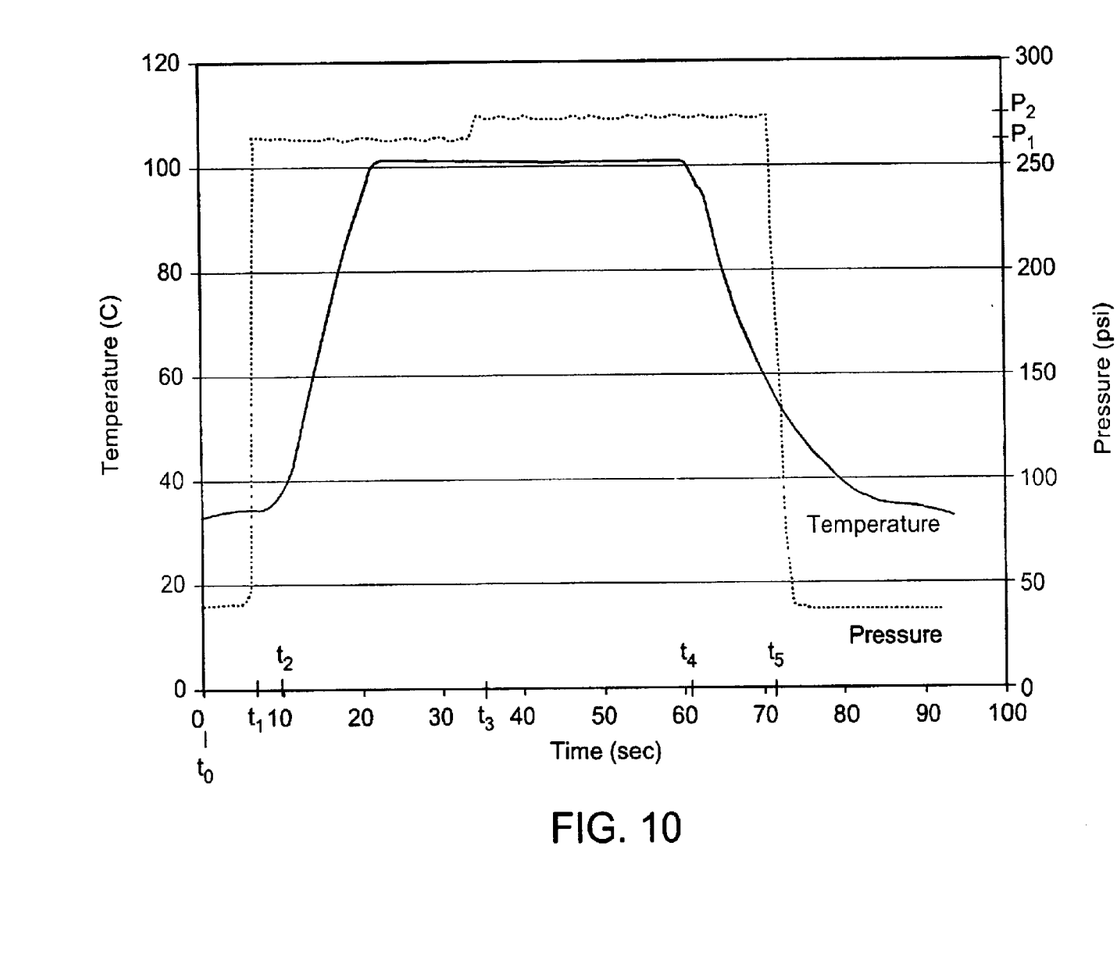
FIG. 10 is a plot of parison internal temperature (Celsius) vs. time (second) and pressure (psi) vs. time (second) during fabrication of a 6-4 medical balloon.

Referring FIG. 10, temperature and pressure profiles during fabrication of the 6-4 balloon are shown. The temperature profile shows an internal parison temperature, as measured by a thermocouple inserted through one end of the parison and positioned in the center of the parison. At $t_0$, the parison was connected to the grippers, and the applied pressure was relatively low, e.g., about 37 psi. At $t_1$, which corresponds to the closing of the upper half of the mold, the pressure was increased to a first balloon forming pressure ($P_1$), here, about 265 psi. Then, at $t_2$, the heater was turned on and controlled to provide balloon forming temperatures, here, an internal parison temperature of about 101° C., to form the balloon. About midway through balloon formation ($t_3$), here, about 35 seconds, the pressure was increased to a second balloon forming pressure ($P_2$), here, about 273 psi. In the present example, about midway through balloon formation, the temperature, as measured by the thermocouple of the lower half shell, was also increased, e.g., stepped from about 123° C. to about 132° C., to maintain the internal parison temperature of about 101° C. Other manufacturing configurations may not require a change in pressure and/or temperature. It is believed that the changes in pressure and temperature helped to fully expand the parison to contact the mold and complete balloon formation. The parison was held at the balloon forming pressures and temperatures for a time sufficient to form the balloon. At a predetermined time ($t_4$), the temperature was decreased, e.g., to room temperature, while the pressure was maintained at the second balloon forming pressure, $P_2$. At $t_5$, the pressure was decreased. The balloon was then removed from the mold and the grippers.

To qualitatively characterize the degree of stress in the balloon, the formed balloon was evaluated by directing polychromatic white light through the balloon, and viewing the balloon with a polarizing lens. In some embodiments, the birefringence pattern generally contains straight and uniform strain lines with minimal taper. FIG. 2A shows the birefringence pattern of a 6-4 balloon formed by the methods described above. In comparison, as shown in FIGS. 2B and 2C, 6-4 balloons in which axial movement was restricted during blowing, e.g., by mechanically restricting the ends of the parison, have birefringence patterns that are non-uniform and not straight, indicating that the balloons have residual stress and/or are tapered.

EXAMPLE 3

The following illustrates formation of an 8-4 (i.e., 8 mm O.D. and 4 cm long) Arnitel® (EM740 from DSM Engineering Plastics) balloon.

A tube of Arnitel® was provided having an inner diameter of about 0.108 cm (0.0425 in), an outer diameter of about 0.203 cm (0.080 in), and a length of about 30.48 cm (12 in). The tube was sealed on one end by heating and pressing the end with pliers. Similar to Example 2, the tube was formed into a parison by axially drawing the open end of the tube at room temperature. The draw rate was about 0.41 cm/sec (0.16 in/sec); the draw length was about 12.065 cm (4.75 in); and the maximum internal nitrogen pressure was about 410 psi. A stretched portion about 12.065 cm (4.75 in) long and having an O.D. of about 0.175 cm (0.069 in) was produced.

Figure 11:
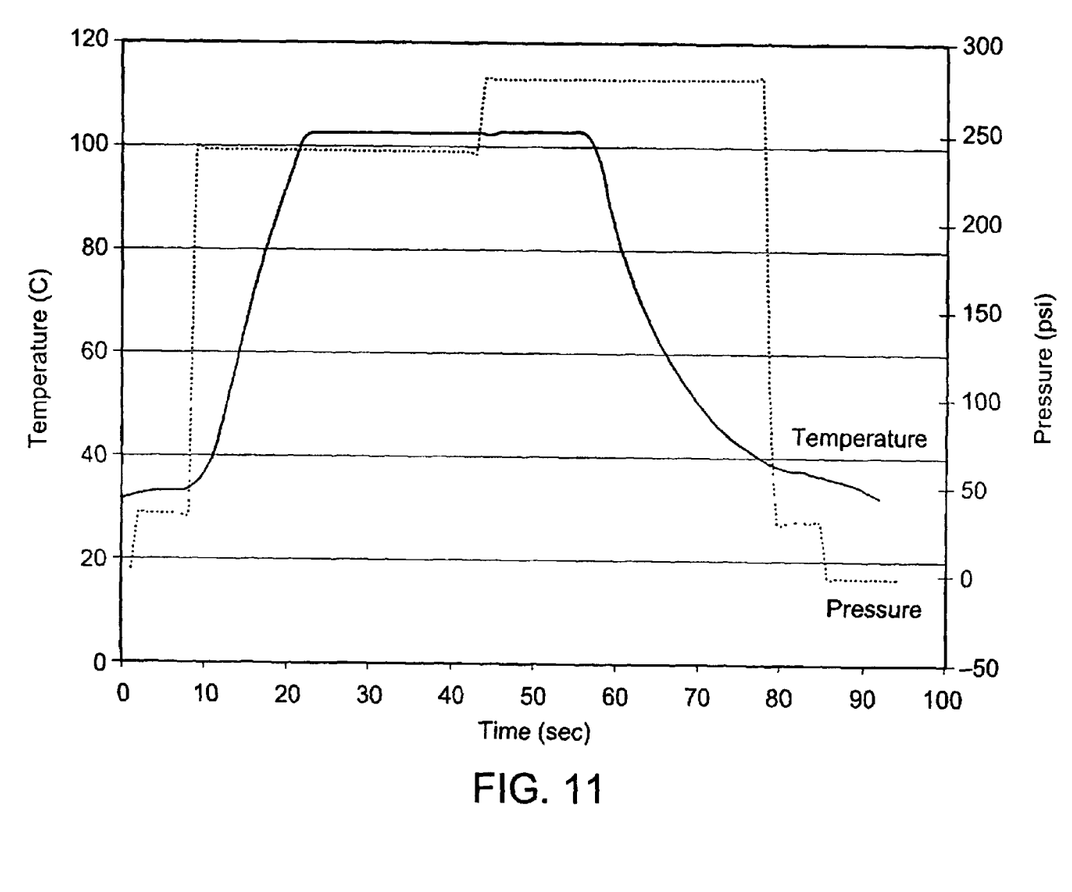
FIG. 11 is a plot of parison internal temperature (Celsius) vs. time (second) and pressure (psi) vs. time (second) during fabrication of an 8-4 medical balloon.

The parison was formed into a balloon using generally the same assembly and method as described in Examples 1 and 2 (with a different mold). FIG. 11 shows the temperature and pressure profiles during blowing of the 8-4 balloon.

The formed balloon was characterized using birefringence to qualitatively evaluate the degree of stress in the balloon.

Other embodiments are within the claims.

What is claimed is:

1. A method of making a medical balloon, comprising:
providing a polymer tube suitable for being formed into the medical balloon, the tube having two ends;
drawing the tube axially; and
expanding the tube radially while allowing the ends of the tube to move axially in response to said radial expansion.

2. The method of claim 1, wherein the tube is below a glass transition temperature of a material of the tube during drawing.

3. The method of claim 2, wherein the tube is below about 100° C. during drawing.

4. The method of claim 1, wherein the tube is internally pressurized during drawing.

5. The method of claim 1, wherein expanding the tube comprises heating the tube.

6. The method of claim 5, wherein the tube is heated to a temperature about equal to or greater than a glass transition temperature of a material of the tube.

7. The method of claim 1, wherein the tube is expanded to an expanded diameter about 5 to 9 times larger than an unexpanded diameter of the tube.

8. The method of claim 1, wherein expanding the tube comprises simultaneously heating and pressurizing the tube.

9. The method of claim 1, wherein expanding the tube comprises:
positioning the tube into a mold; and
simultaneously heating and pressurizing the tube.

10. The method of claim 1, wherein expanding the tube comprises contacting the tube with a liquid.

11. The method of claim 10, wherein the liquid comprises water.

12. The method of claim 1, wherein the ends of the tube are allowed to move axially a distance between about 5 and about 30 percent of an original length of the tube.

13. The method of claim 1, wherein the tube is formed of a polymer having regions of different hardnesses.

14. The method of claim 1, wherein the tube comprises a block copolymer including hard segments and soft segments.

15. The method of claim 14, wherein the block copolymer comprises a material selected from a group consisting of a polyether-ester elastomer, a polyester elastomer, and a polyether block amide.

16. The method of claim 14, wherein the block copolymer comprises a polyether-ester elastomer.

17. The method of claim 1, wherein the tube comprises a material selected from a group consisting of a polyester and a polyamide.

18. The method of claim 1, wherein the tube is a multi-layer tube.

19. The method of claim 1, wherein the tube is a coextruded tube having layers of different hardnesses.

20. The method of claim 1, further comprising characterizing the balloon by birefringence.

21. The method of claim 1, further comprising attaching the balloon to a catheter to form a balloon catheter device.

22. The method of claim 1, further comprising sterilizing the balloon by heating between about 32° C. and about 60° C.

23. The method of claim 1, wherein expanding the tube radially comprises allowing the ends of the tube to move inwardly in response to said radial expansion.

24. A method of making a medical balloon, comprising:
providing a polymer tube suitable for being formed into the medical balloon, the tube having two ends; and
expanding the tube radially while allowing the ends of the tube to move axially in response to said radial expansion.

25. The method of claim 24, further comprising axially orienting a material of the tube.

26. The method of claim 25, wherein axially orienting the material comprises axially drawing the tube.

27. The method of claim 26, wherein axially orienting the material further comprises internally pressurizing the tube.

28. The method of claim 24, wherein expanding the tube comprises contacting the tube with a liquid.

29. The method of claim 28, wherein the liquid comprises water.

30. The method of claim 24, wherein expanding the tube comprises:
heating the tube to a temperature about equal to or greater than a glass transition temperature of a material of the tube; and
introducing a gas into the tube.

31. The method of claim 24, wherein expanding the tube further comprises placing the tube into a mold.

32. The method of claim 24, wherein the tube comprises a block copolymer.

33. The method of claim 24, further comprising characterizing the balloon by birefringence.

34. The method of claim 24, further comprising attaching the balloon to a catheter to form a balloon catheter device.

35. The method of claim 1, further comprising positioning a stent on the balloon.

36. The method of claim 24, further comprising positioning a stent on the balloon.

* * * * *